(12) United States Patent
Sun et al.

(10) Patent No.: US 8,990,137 B2
(45) Date of Patent: Mar. 24, 2015

(54) APPARATUS FOR MEMRISTOR/NEURON EMULATION AND TESTING

(71) Applicant: Board of Governors for Higher Education, State of Rhode Island and Providence Plantations, Providence, RI (US)

(72) Inventors: Ying Sun, West Warwick, RI (US); Robert Rieger, Kaohsiung (TW)

(73) Assignee: Rhode Island Board of Education, State of Rhode Island and Providence Plantations, Providence, RI (US)

( * ) Notice: Subject to any disclaimer, the term of this patent is extended or adjusted under 35 U.S.C. 154(b) by 29 days.

(21) Appl. No.: 13/853,924

(22) Filed: Mar. 29, 2013

(65) Prior Publication Data

US 2014/0039862 A1     Feb. 6, 2014

Related U.S. Application Data

(60) Provisional application No. 61/617,111, filed on Mar. 29, 2012.

(51) Int. Cl.
| G06F 17/00 | (2006.01) |
| G06F 19/12 | (2011.01) |
| G06N 3/063 | (2006.01) |

(52) U.S. Cl.
CPC .............. *G06F 19/12* (2013.01); *G06N 3/0635* (2013.01)
USPC ........................................................... 706/45

(58) Field of Classification Search
USPC ............................................ 706/1, 12, 45, 62
See application file for complete search history.

(56) References Cited

U.S. PATENT DOCUMENTS

| 5,508,529 A * | 4/1996 | Roenker et al. ................. 257/14 |
| 2009/0043722 A1* | 2/2009 | Nugent ........................... 706/25 |
| 2012/0150781 A1* | 6/2012 | Arthur et al. .................... 706/35 |

* cited by examiner

*Primary Examiner* — David Vincent
(74) *Attorney, Agent, or Firm* — Gesmer Updegrove LLP

(57) ABSTRACT

A method and a device are disclosed for an electronic neuron emulator for representing both passive and active electrical properties of a live neuron. The currents used to generate action potentials are derived from a pre-charged capacitor. The present invention provides for a more physiological state for testing neuroscience instruments such as the single-electrode voltage clamp and the patch clamp. The device can also include multiple pre-charged capacitors to represent ionic channels with more accurate physiologically parameters.

11 Claims, 6 Drawing Sheets

Stage 1. Resting Potential
(S1 & S2 on; S3 off)

Stage 2. Action Potential
(S1 & S2 off; S3 on)

APPARATUS FOR MEMRISTOR/NEURON EMULATION AND TESTING

BACKGROUND OF THE INVENTION

The standard device for testing electronic neuroscience instruments such as a voltage clamp amplifier is a simple resistor-capacitor (RC) circuit. While the RC circuit can represent the passive electrical properties of a live neuron, it cannot generate action potentials to interact with the voltage clamp amplifier in a dynamic way.

Previously, Breau et al developed a neuron emulator that used an oscillator to generate the action potentials. The oscillator was a time-varying voltage source, which was too strong to overcome by use of a voltage clamp amplifier. Therefore, it was not possible to voltage-clamp the action potentials generated by this device.

The neuron emulator in the present invention uses a novel concept, whereby an action potential is generated by switching a pre-charged capacitor into the output circuitry. Once the capacitor is discharged, it is switched out of the output circuitry and charged up for the next firing of the action potential. The present invention overcame the previous limitations of the neuron emulator.

BRIEF DESCRIPTION OF THE DRAWING

The following description may be further understood with reference to the accompanying drawing in which.

DETAILED DESCRIPTION OF THE INVENTION

The present invention discloses an electronic neuron emulator for a single-electrode setting that is capable of having passive properties (membrane resistance and capacitance) and the active properties (action potential) of a live neuron. A novel design feature of this invention is that the currents used to generate action potentials come from a pre-charged capacitor. Unlike a voltage source or a current source, the charge on the capacitor is limited, thereby providing a more realistic physiological condition for testing existing neuroscience instruments such as the single-electrode voltage clamp and the patch clamp.

Figure 1:
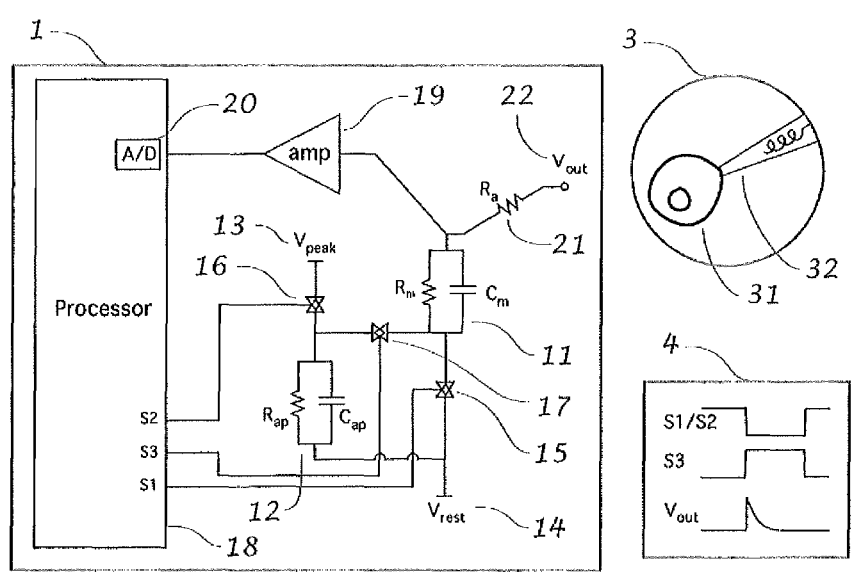
FIG. 1 shows an illustrative diagrammatic view of the neuron emulator with which techniques of the invention may be employed.

FIG. 1 shows the circuit diagram of the neuron emulator in 1. A patch clamp setting 3 shows the circuit that it emulates. The switching signals and the resulting action potential output of the neuron emulator are represented in 4. The passive properties of the neuron are represented by the circuit of $R_m$ in parallel with $C_m$, $R_m$-$C_m$ circuit 11. The $R_m$-$C_m$ circuit 11 is connected to a voltage reference representing the resting membrane potential $V_{rest}$ 14. The active properties of the neuron are represented by the circuit of $R_{ap}$ in parallel with $C_{ap}$, $R_{ap}$-$C_{ap}$ circuit 12. The active properties circuit is intermittently connected to $V_{peak}$ 13 for pre-charging.

To activate an action potential, the $R_{ap}$-$C_{ap}$ circuit 12 undergoes switching in series with the $R_m$-$C_m$ circuit 11. After discharging, the $R_{ap}$-$C_{ap}$ circuit 12 switches out and the $R_m$-$C_m$ circuit 11 connects to the resting membrane potential $V_{rest}$ 14. The switching operation employs three switches, S1 15, S2 16, and S3 17. All three switches are controlled by a microprocessor 18. The output of the $R_m$-$C_m$ circuit 11 is sent to the analog-to-digital converter 20 via an amplifier 19. The microprocessor 18 constantly monitors the membrane potential and adjusts the firing rate accordingly. The output of the $R_m$-$C_m$ circuit 11 represents the membrane potential of the neuron. The output of the $R_m$-$C_m$ circuit 11 is accessed externally via resistor $R_a$ 21 as the output voltage $V_{out}$ 22, where $R_a$ 21 represents the resistance of the electrode. The timing of the switching signals (4) is done is such as way that the action potential is generated by turning S1 and S2 off and S3 on. The timing of the switching signals 4 generates the action potential by turning S1 15 and S2 16 off and turning S3 17 on.

Figure 2:
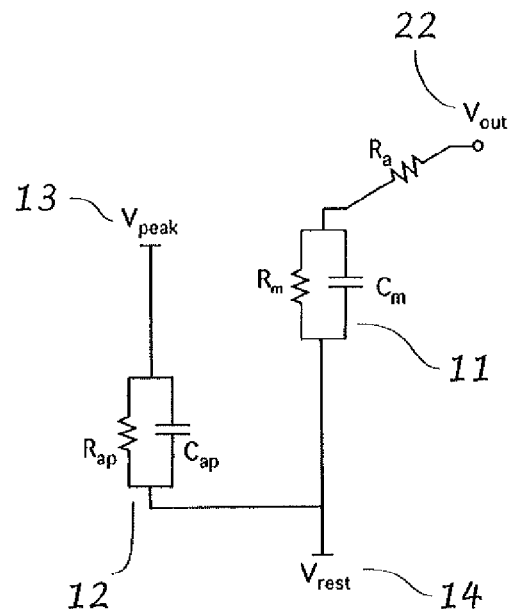
FIG. 2 shows an illustration of resting potential and action potential of the neuron emulator.
Figure 2:
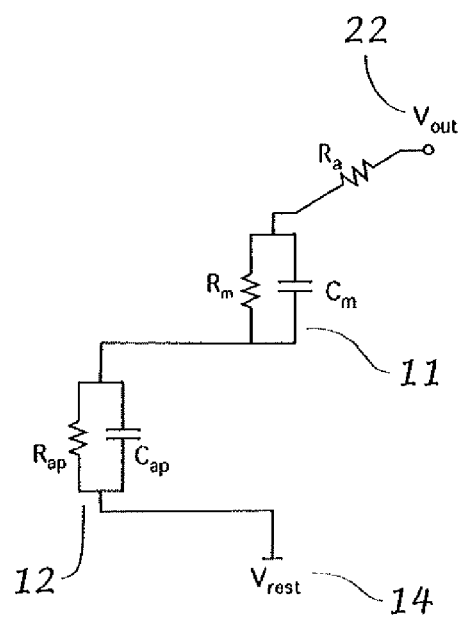

FIG. 2 further describes the switching of the $R_{ap}$-$C_{ap}$ circuit 12 in two positions, Stage 1 and Stage 2. Stage 1 represents the resting potential where S1 15 and S2 16 are turned on and S3 17 turned off. In Stage 1, the $R_{ap}$-$C_{ap}$ circuit 12 is disconnected from the $R_m$-$C_m$ circuit 11 and is charged by $V_{peak}$ 13. Stage 2 represents the action potential where S1 15 and S2 16 turned off and S3 17 turned on. In the Stage 2, the $R_{ap}$-$C_{ap}$ circuit 12 is connected in series with the $R_m$-$C_m$ circuit 11. The output $V_{out}$ 22 momentarily jumps to $V_{peak}$ 13 and then discharges. The firing of consecutive action potentials is accomplished by alternating between Stage 1 and Stage 2.

Surprisingly, the aforementioned neuron emulator produces an action potential that has the waveform of a simple exponential discharge. The waveform is further improved to be more representative of a real action potential than previously.

Figure 3:
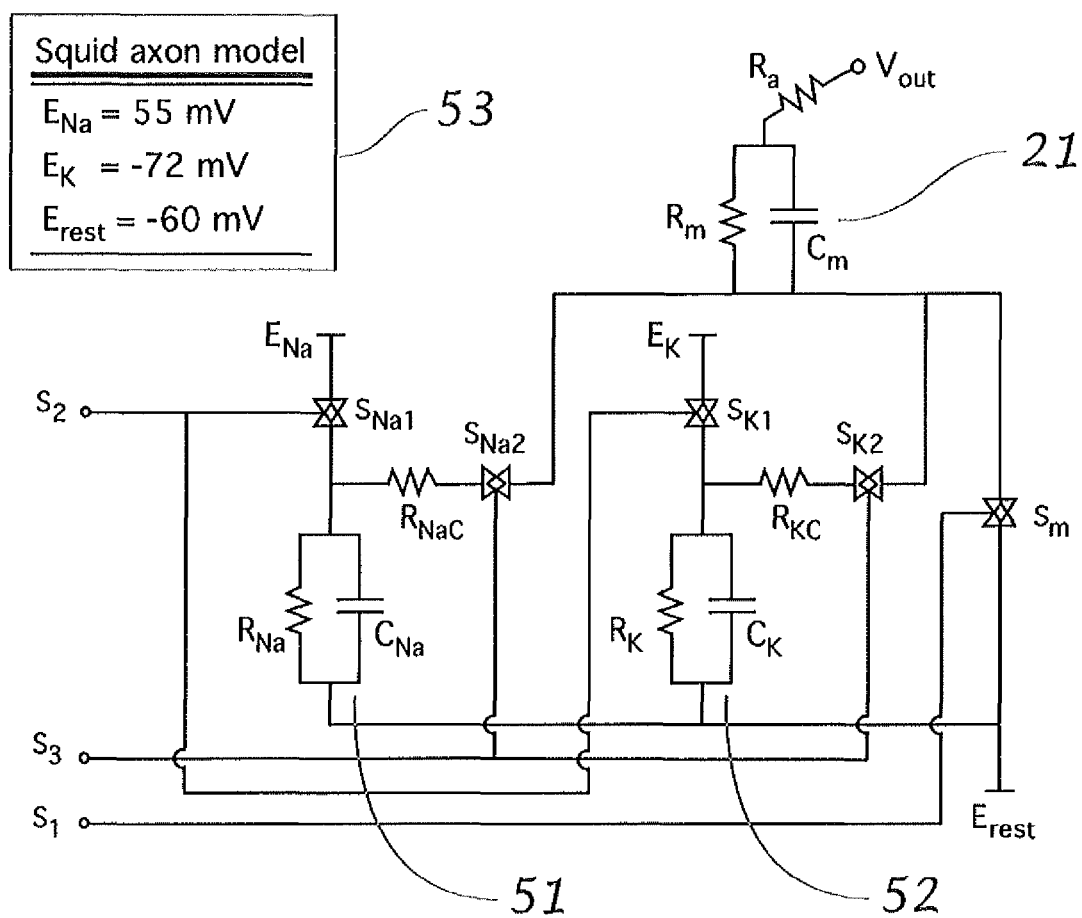
FIG. 3 shows two RC circuits in parallel to generate the action potential.

FIG. 3 shows another embodiment of the present invention using two RC circuits in parallel to generate the action potential. Furthermore, the circuit elements are adjusted to physiological states of relevance. In the disclosed embodiment, the example represents the squid giant axon with physiological parameters 53 described by Hodge and Huxley. In this embodiment, the $R_{Na}$-$C_{Na}$ circuit 51 represents the sodium channel and the $R_K$-$C_K$ circuit 52 represents the potassium channel. Any other physiological variation or state is possible by tuning the circuit parameters, adding additional R-C circuits, or a combination of both to represent different ionic channels for the generation of action potentials.

EXAMPLE 1

Demonstration of Neuron Emulator Device

Figure 4:
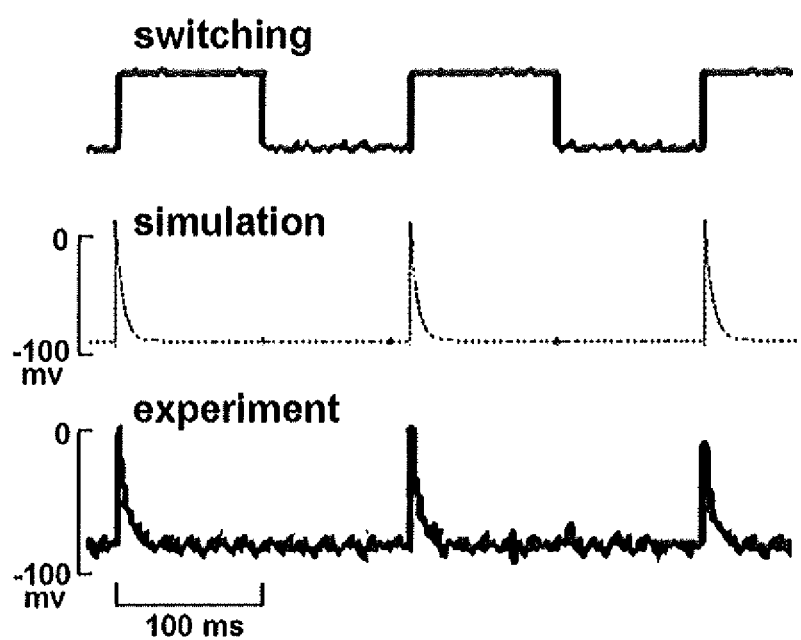
FIG. 4 shows the switching signal, the computer-simulated action potential and the resultant action potential generated by the neuron emulator.

The neuron emulator was constructed using a single R-C circuit as described above. FIG. 4 shows the results of a study where the functionality of the neuron emulator is demonstrated. In the demonstration, the switching signal, the computer-simulated action potential and the resultant action potential generated by the neuron emulator device are shown. Remarkably, the action potential was uniformed reproduced by the device in several switching.

Figure 5:
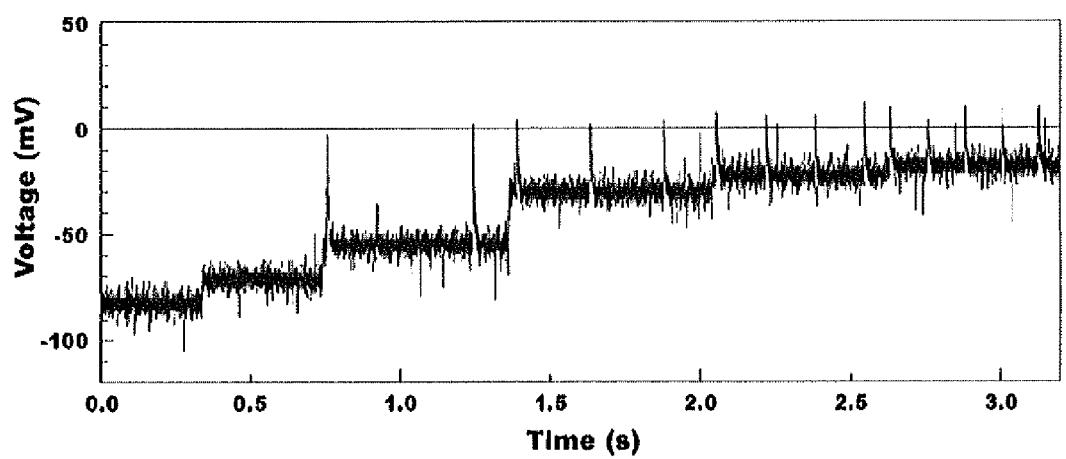
FIG. 5 shows a step clamp experiment with the neuron emulator.

FIG. 5 shows the result of a step clamp experiment with the neuron emulator. The firing rate of the action potential was increased as the membrane potential was raised by the externally injected current.

Figure 6:
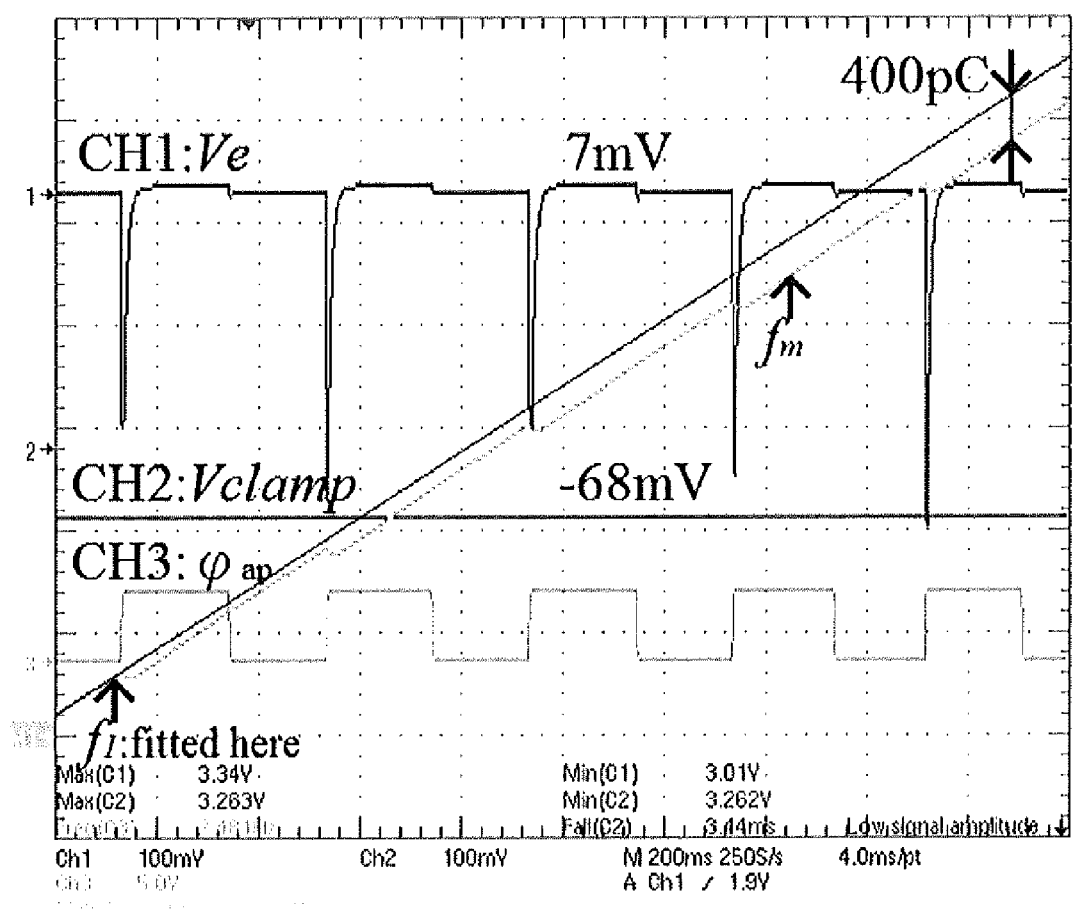
FIG. 6 shows an annotated screen shot of an oscilloscope during a voltage clamp experiment.

FIG. 6 is an annotated screen shot of an oscilloscope during a voltage clamp experiment. A commercial voltage clamp amplifier was connected to the neuron emulator and successfully implemented a voltage clamp. An action potential was generated at each on-set of the switching signal shown on channel 3 (CH3). The output voltage was successfully clamped to a constant voltage as shown on channel 2 (CH2). The feedback current responsible for canceling out the action potential was shown on channel 1 (CH1).

Those skilled in the art will appreciate that numerous modifications and variations may be made to the above disclosed embodiments without departing from the spirit and scope of the inventions.

The invention claimed is:

1. An apparatus for emulating the passive and active electrical properties of a neuron comprising:
   a. a switching circuit;
   b. at least two interconnected circuits including a first resistor-capacitor circuit and a second pre-charged resistor-capacitor circuit;
   c. said switching circuit to alter the connectivity of the at least two interconnected circuits;
   d. a processor to monitor a membrane potential in the first resistor-capacitor circuit;
   e. said processor to control the firing of an action potential using the switching circuit, wherein the source of the action potential is from the charge initially stored on a capacitor in second pre-charged resistor-capacitor circuit; and
   f. an output from the first resistor-capacitor circuit using a resistor for an electrode resistance.

2. The apparatus of claim 1, wherein an algorithm is implemented in the processor to control the firing rate of the action potential based on the membrane potential.

3. The apparatus of claim 1, further comprising a third resistor-capacitor circuit.

4. The apparatus of claim 1, wherein said switching circuit includes three switches.

5. The apparatus of claim 4, wherein said action potential is generated by turning selected switches on and off.

6. The apparatus of claim 1, wherein switching of said switching circuit comprises two stages.

7. The apparatus of claim 6, wherein a first stage includes a configuration in which said second pre-charged resistor-capacitor circuit is disconnected from said first resistor-capacitor circuit.

8. The apparatus of claim 7, wherein a second stage includes a configuration in which said second pre-charged resistor-capacitor circuit is connected with said first resistor-capacitor circuit.

9. The apparatus of claim 8, wherein said firing of an action potential is accomplished by alternating between said first stage and said second stage.

10. The apparatus of claim 3, wherein said second pre-charges resistor-capacitor circuit and said third resistor-capacitor circuit each represent different ionic channels to generate action potentials.

11. The apparatus of claim 3, wherein said third resistor-capacitor circuit is pre-charged.

* * * * *